United States Patent [19]

Kuthan et al.

[11] 3,969,359

[45] July 13, 1976

[54] METHOD OF PREPARING N-SUBSTITUTED 3,5-DICYAN-1,4-DIHYDROPYRIDINES

[75] Inventors: Josef Kuthan; Jaroslav Paleček; Miroslav Šrámek, all of Prague, Czechoslovakia

[73] Assignee: Vysoka skola chemicko-technologicka, Prague, Czechoslovakia

[22] Filed: Sept. 11, 1974

[21] Appl. No.: 505,006

[30] Foreign Application Priority Data

Sept. 18, 1973 Czechoslovakia .................. 6416-73

[52] U.S. Cl. ............................................ 260/294.9
[51] Int. Cl.² ........................................ C07D 213/57
[58] Field of Search ................................. 260/294.9

[56] References Cited
OTHER PUBLICATIONS

Fieser & Fieser, Reagents for Organic Synthesis, vol. 1, pp. 300, 1078, 1079, Wiley Pub. (1967).
Fieser & Fieser, Reagents for Organic Synthesis, vol. 2, p. 383, Wiley Interscience, (1969).

*Primary Examiner*—Alan L. Rotman

[57] ABSTRACT

A method for preparing N-substituted 3,5-dicyan-1,4-dihydropyridines designed for use as radioactive radiation detectors in scintillation techniques is described. The method involves reacting an unsubstituted dihydropyridine derivative in an aprotic polar solvent with an alkali metal or alkaline earth metal hydride or amide and, subsequently, alkylating the resultant product.

9 Claims, No Drawings

METHOD OF PREPARING N-SUBSTITUTED 3,5-DICYAN-1,4-DIHYDROPYRIDINES

The present invention relates to a method for preparing N-substituted 3,5 dicyan-1,4-dihydropyridines. More particularly, the present invention relates to a method for preparing N-substituted 3,5-dicyan-1,4-dihydropyridines by alkylation of the corresponding unsubstituted dihydropyridine.

N-substituted 3,5-dicyan-1,4-dihydropyridines are widely used commercially in scintillation applications as detectors of radioactive radiation, either in the form of mono-crystalline materials or as liquid or solid solutions as described in Czechoslovakian Pat. No. 141,300. The feasibility of utilizing these compositions in such applications is dependent upon obtaining large yields in the preparative process, an end not attained with any degree of uniformity heretofore.

The pyridines contemplated herein are of the general formula

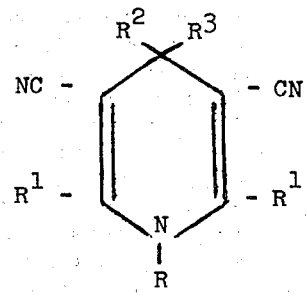

wherein R is selected from among alkyl radicals having from 1–6 carbon atoms, cycloalkyl radicals having from 5–8 carbon atoms and an aralkyl having 1–3 carbon atoms in the alkyl chain and from 6–10 carbon atoms in the aryl residue, $R^1$ is selected from among alkyl radicals having from 1–2 carbon atoms, an unsubstituted phenyl group and an alkyl substituted phenyl group in which the alkyl has from 1–2 carbon atoms, $R^2$ is selected from among hydrogen, an alkyl radical having from 1–3 carbon atoms and a complex formed with the following $R^3$ group, said complex having from 4–7 carbon atoms, and $R^3$ is selected from among alkyl radicals having from 1–3 carbon atoms, an unsubstituted phenyl group and an alkyl substituted phenyl group in which the alkyl has from 1–2 carbon atoms.

Various techniques for preparing compounds within the scope of the aforementioned generic formulation are known in the art. See for example J. Chem. Soc., 1968, Page 1675. Unfortunately, many of these prior art processes have not been commercially viable due to unsatisfactory yields ranging from 16–30 per cent. A recent effort aimed at overcoming the yield limitation is described in Czechoslovakian patent application No. PV 9188-71. However, the product obtained in accordance with the procedure described therein required a plurality of crystallization steps to yield a purified product, or in the case of 3-substituted-3-(N-substituted amino) acrylonitriles, a vacuum distillation purification step. Thus, it is apparent that the added purification steps required to produce commercially acceptable yields necessitate the use of burdensome equipment and increases the economics of the process.

Accordingly, it is an object of the present invention to describe a method for preparing N-substituted 3,5 dicyan-1,4-dihydropyridines which obviates the prior art limitations and minimizes the economic requirements.

In accordance with the present invention, this end is successfully attained by a procedure wherein the unsubstituted dihydro derivative is successively reacted in an aprotic solvent with (a) an alkali metal, an alkaline earth metal hydride and/or an alkali metal amide, and (b) an alkylating agent at a temperature ranging from 0°–70°C, the resulting molar ratio of the components being 1:1.0 to 1.5:1.0 to 1.5 in accordance with equation (1) as follows:

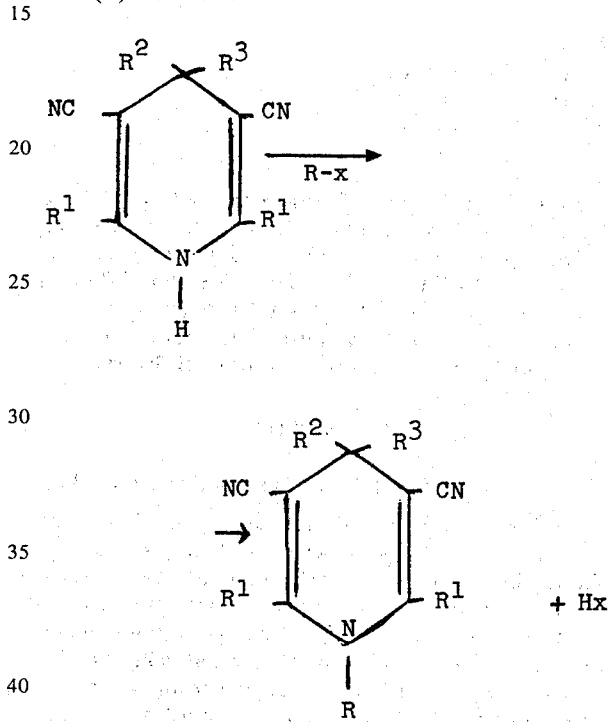

In the practice of the present invention, lithium, sodium and potassium hydrides and/or amides have been found most suitable as the alkali metals whereas calcium has been found to be the most advantageous alkaline earth metal in the alkaline earth metal hydride.

The aprotic polar solvents chosen for use herein may be selected from among acid amides, cyclic ethers, N-methylmorpholine, dimethylsulfoxide and tetramethylenesulphone. Typical acid amides include hexamethylphosphortriamide, dimethylformamide, dimethylacetamide, N-methylpyrrolidone and tetramethylcarbamide. Suitable cyclic ethers for this purpose are dioxane and ethyleneglycol dimethylether.

The alkylation agent referred to as R-x in equation 1 may be a halide wherein the x component is a halogen atom and the R component is a radical as described above in connection with the generic formulation. Additionally, the alkylation agent may be chosen from among sulfuric or sulfonic acid esters or esters of chloroformic acid.

As indicated above, the source material for the dihydropyridines described herein is a non-alkylated 1,4-dihydropyridine. This compound may conveniently be obtained by means of well-known chemical processes, i.e. as described in Chem. Rev. Volume 72, 1972, Page 1. In such processes, the corresponding 3-substituted- 3-aminoacrylonitriles are reacted with carboxylic compounds in an acidic medium as shown in equation (2) below:

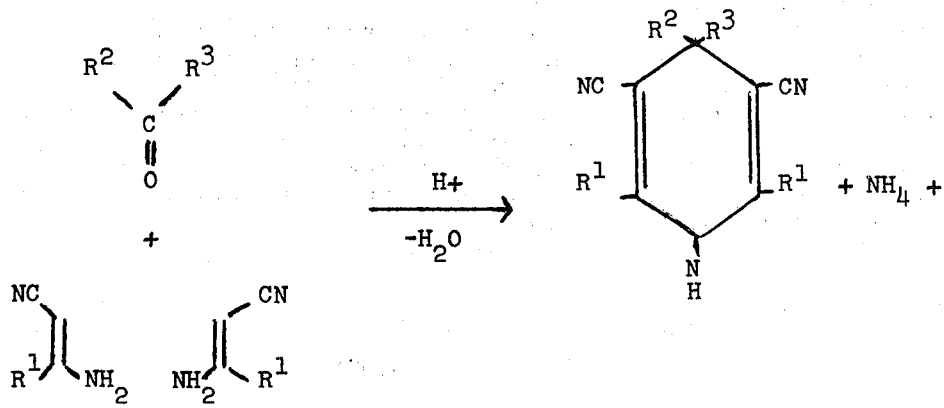

wherein $R^1$, $R^2$ and $R^3$ represent the radicals defined herein-above with respect to the generic formulation.

The invention will be more readily understood by those skilled in the art by reference to the following exemplary embodiments. It will be appreciated that these embodiments are set forth merely for purposes of exposition and are not to be construed as limiting.

EXAMPLE I 1,2,4,4,6-pentamethyl-3,5-dicyan-1,4-dihydropyridine

A solution was prepared by admixture of 374 parts by weight of 2,4,4,6-tetramethyl-3,5-dicyan-1,4-dihydropyridine with 1500 parts by volume of hexamethylphosphortriamide. Next, 55 parts by weight of sodium hydride were added to the resultant solution under external cooling by ice and water while being steadily agitated over a time period ranging from 1–2 hours. The resultant mixture was then agitated for an additional 4 hours at ambient temperature and, after cooling, 282 parts by weight of methyl iodide were added dropwise. The mixture was then agitated for 5 hours at temperatures ranging from 35°–40°C and poured into a quadruple volume of ice water. The desired product was then removed and recrystallized out of ethanol. The yield was found to be 326 parts by weight (81.1%) and the product evidenced a melting point within the range of 166°–168°C.

EXAMPLE II 1-ethyl-2,4,4,6-tetramethyl-3,5-dicyan-1,4-dihydropyridine

This Example describes alternative techniques for preparing the noted compound, such alternatives being designated (a), (b) and (c), respectively.

a. A solution of the sodium salt of 2,4,4,6-tetramethyl-3,5-dicyan-1,4-dihydropyridine was prepared by admixing 375 parts by weight of the dihydro derivative thereof with 55 parts by weight of sodium hydride in 1600 parts by volume of dimethyl sulfoxide. Next, 368.4 parts by volume of diethyl sulfate were added to the solution under external cooling with ice and water while being steadily agitated. After 6 hours of agitation at ambient temperature, the reaction admixture was processed by conventional techniques, so yielding 345 parts by weight (78.8%) of the desired product which evidenced a melting point ranging from 152°–154°C (as recrystallized out of ethanol).

b. A solution was prepared by admixing 42 parts by weight of 2,4,4,6-tetramethyl-3,5-dicyan-1,4-dihydropyridine with 200 parts by volume of dimethylformamide. Next, 7.5 parts by weight of sodium hydride under external cooling by ice and water was added to the solution over a 30 minute time period under steady agitation. The reaction mixture was then agitated for 3 hours at room temperature and, after cooling again, 25.5 parts by volume of ethyl iodide were added thereto. Agitation was continued for 6 hours at ambient temperature. Following, the solvents were evaporated in vacuo and 40 parts by volume of cool water added to the residue. The desired product was then recovered and recrystallized from ethanol. A yield of 38 parts by weight (77.3%) of the desired product was attained, the product evidencing a melting point ranging from 152°–153°C.

c. A solution was prepared by admixing 31.2 parts by weight of 2,4,4,6-tetramethyl-3,5-dicyan-1,4-dihydropyridine, 150 parts by volume of N-methylpyrrolidone and 50 parts by volume of benzene. Next, 25 parts by weight of lithium diisopropylamide was added to the solution over a 2 hour period under external cooling of the reaction mixture. Then, the mixture was heated for 3 hours to a temperature within the range of 35°–45°C and after cooling, 25.4 parts by weight of ethyl bromide were added thereto. Recovery of the desired product was then effected by conventional means, so yielding 23.1 parts by weight of product.

EXAMPLE III 1-ethyl-2,6-dimethyl-4-phenyl-3,5-dicyan-1,4-dihydropyridine

A solution was prepared by admixing 32.56 parts by weight of 2,6-dimethyl-4-phenyl-3,5-dicyan-1,4-dihydropyridine with 150 parts by volume of dimethylformamide. 4.5 parts by weight of sodium hydride were then added to the solution while agitating it and in the presence of ice. After a period of 4 hours of agitation at room temperature, the reaction mixture was cooled and 15.2 parts by volume of ethyl iodide added thereto. Agitation was then continued for an additional 6 hours at a temperature within the range of 30°–35°C. The desired product was recovered by recrystallization from ethanol, a yield of 85.1% or 31.0 parts by weight resulting. The product evidenced a melting point within the range of 171°–172°C.

EXAMPLE IV 1-ethyl-2,6-diphenyl-4-methyl-3,5-dicyan-1,4-dihydropyridine 17.8 parts by weight of 2,6-diphenyl-4-methyl-3,5-dicyan-1,4-dihydropyridine were dissolved in 150 parts by volume of dimethylformamide (partly in suspension). Then, 2.0 parts by weight of sodium hydride were added thereto over a time period of 35 minutes under external cooling with ice and while agitating the mixture. Following, the mixture was agitated for 4.5 hours at ambient temperatures and again cooled. Then, 6.7 parts by volume of ethyl iodide were added to the reaction mixture and agitation continued for 5 hours. The desired product was recovered by conventional techniques in an amount of 13.1 parts by weight (67.3% yield) and evidenced a melting point within the range of 188°–189°C.

EXAMPLE V 1-hexyl-2,6-dimethyl-4-ethyl-3,5-dicyan-1,4-dihydropyridine

A solution of the sodium salt of 2,6-dimethyl-4-ethyl-3,5-dicyan-1,4-dihydropyridine was prepared by admixing 37.4 parts by weight of dihydropyridine and 5.5 parts by weight of sodium hydride in 175 parts by volume of tetramethylene sulphone. Then, 41.3 parts by volume of hexyl iodide were added thereto with agitation and under external cooling. The desired product was recovered by conventional techniques in an amount of 30.75 parts by weight (56.7% yield).

EXAMPLE VI 1-benzyl-2,4,4,6-tetramethyl-3,5-dicyan-1,4-dihydropyridine

To the solution prepared from admixing 37.4 parts by weight of 2,4,4,6-tetramethyl-3,5-dicyan-1,4-dihydropyridine, 7 parts by volume of dioxane and 8 parts by volume of dimethyl formamide were added. Following, 0.55 parts by weight of sodium hydride was added thereto over a period of 1 hour while agitating the mix under external cooling with ice. The resultant mixture was then agitated for 3 hours at 30°C and recooled. Then, 3.23 parts by volume of benzyl chloride were added thereto and recovery of the desired product effected by conventional techniques. 4.41 parts by weight (79.4% yield) of the product resulted, such product evidencing a melting point within the range of 133°–134°C.

EXAMPLE VII 1-ethyl-2,6-dimethyl-4,4-tetramethylene-3,5-dicyan-1,4-dihydropyridine To the solution prepared from 21.3 parts by weight of 2,6-dimethyl-4,4-tetramethylene-3,5-dicyan-1,4-dihydropyridine and 120 parts by volume of hexamethylphosphortriamide was added 2.64 parts by weight of sodium hydride under external cooling with agitation over a period of 1 hour. Agitation was then continued for 5 hours and after again cooling, 8.9 parts by volume of ethyl iodide were added thereto. Recovery of the desired product in an amount of 19.56 parts by weight (81.2% yield) was then effected by conventional techniques. The product evidenced a melting point within the range of 101°–102°C.

While the invention has been described in the foregoing exemplary embodiments in terms of preparing various N-substituted 3,5-dicyan-1,4-dihydropyridines, it will again be appreciated that it is not intended to be limited to the specific details disclosed therein, modification thereto being readily made without departing from the spirit and scope of the invention.

What is claimed is:

1. Method for the preparation of N-substituted 3,5-dicyan-1,4-dihydropyridines of the general formula

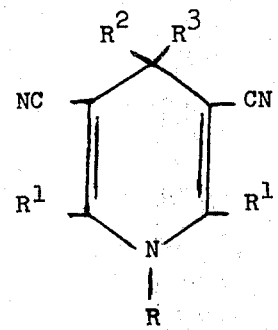

wherein
R represents a radical selected from the group consisting of (a) alkyl groups having from 1–6 carbon atoms, (b) cycloalkyl groups having from 5–8 carbon atoms and (c) aralkyl groups having 1–3 carbon atoms in the alkyl chain and from 6–10 carbon atoms in the aryl radical,
$R^1$ represents a radical selected from the group consisting of (a) alkyl groups having from 1–2 carbon atoms, (b) an unsubstituted phenyl group and (c) a phenyl group having alkyl substituents thereon containing from 1–2 carbon atoms,
$R^2$ represents a radical selected from the group consisting of (a) hydrogen, (b) alkyl groups having from 1–3 carbon atoms and (c) a complex containing 4–7 carbon atoms formed with $R^3$, and
$R^3$ represents a radical selected from the group consisting of (a) alkyl groups containing from 1–3 carbon atoms, (b) unsubstituted phenyl groups and (c) a phenyl group bearing alkyl substituents having from 1–2 carbon atoms which comprises the steps of successively
(1) reacting the corresponding unsubstituted dihydro derivative in a polar aprotic solvent with a compound selected from the group consisting of (a) alkali metal hydrides, (b) alkaline earth metal hydrides and (c) an alkali metal amide, and
(2) alkylating the resultant product at a temperature within the range of 0°–70°C, the molar ratio of components ranging from 1:1.0 to 1.5 : 1.0 to 1.5.

2. Method in accordance with claim 1 wherein the alkaline earth metal hydride is calcium hydride.

3. Method in accordance with claim 1 wherein the alkali metal hydride is sodium hydride.

4. Method in accordance with claim 1 wherein the alkylating agent is methyl iodide.

5. Method in accordance with claim 1 wherein the alkylating agent is diethyl sulfate.

6. Method in accordance with claim 1 wherein the alkylating agent is ethyl iodide.

7. Method in accordance with claim 1 wherein the solvent is hexamethylphosphortriamide.

8. Method in accordance with claim 1, wherein alkylation is effected with an alkylation agent selected from the group consisting of an alkyl halide having from 1–6 carbon atoms, benzyl chloride and diethylsulfate.

9. Method in accordance with claim 1, wherein the polar aprotic solvent is selected from the group consisting of (a) hexamethylphosphortriamide, (b) dimethylsulfoxide, (c) dimethylformamide, (d) N-methylpyrrolidone and (e) tetramethylenesulfone.

* * * * *